(12) United States Patent
Coderch Negra et al.

(10) Patent No.: US 8,138,362 B2
(45) Date of Patent: Mar. 20, 2012

(54) METHOD FOR EXTRACTING INTERNAL LIPIDS FROM WOOL USING SUPERCRITICAL FLUIDS

(75) Inventors: Ma Luisa Coderch Negra, Barcelona (ES); Raquel Ramírez Mileo, Barcelona (ES); Meritxell Martí Gelabert, Barcelona (ES); José Luis Parra Juez, Barcelona (ES); Iratxe Garay Peral, Las Carreras (ES); Oscar Salas Vaquero, Leioa (ES); Jorge Álvarez Alcega, Leioa (ES)

(73) Assignee: Centro Technologico Gaiker, Zamudio (ES)

( * ) Notice: Subject to any disclaimer, the term of this patent is extended or adjusted under 35 U.S.C. 154(b) by 283 days.

(21) Appl. No.: 12/529,453

(22) PCT Filed: Feb. 27, 2008

(86) PCT No.: PCT/ES2008/070033
§ 371 (c)(1),
(2), (4) Date: Nov. 18, 2009

(87) PCT Pub. No.: WO2008/104630
PCT Pub. Date: Sep. 4, 2008

(65) Prior Publication Data
US 2010/0099899 A1    Apr. 22, 2010

(30) Foreign Application Priority Data
Mar. 1, 2007 (ES) .................................. 200700543

(51) Int. Cl.
*C11B 1/10* (2006.01)
(52) U.S. Cl. ............................................ 554/8; 554/23
(58) Field of Classification Search ................ 554/8, 23
See application file for complete search history.

(56) References Cited

U.S. PATENT DOCUMENTS 3,619,116 A    11/1971    Saville
4,548,755 A * 10/1985    Stahl et al. .................... 554/8

FOREIGN PATENT DOCUMENTS

| EP | 1201736 B1 * | 4/2005 |
| WO | WO 01/04244 | 1/2001 |
| WO | WO02/100990 | 12/2002 |

OTHER PUBLICATIONS

ES 2204240 (B1), Consejo Superior Investigacion, Method for obtaining lipid fractions from wool or lanolin using pressuized carbon dioxide, 2005, English translation equivalent of WO 02/100990 on 1449, 6 pages.*
L. Coderch et al. "Extraction and analysis of ceramides from internal wool lipids", JAOCS, 2002, vol. 79, No. 12, pp. 1215-1220.
Dominguez et al., "Characterization of supercritical fluid extracts from raw wool by TLC-FID and GC-MS", JAOCS, 2003, vol. 80, No. 7, pp. 717-724.
Lopez-Mesas et al., "Supercritical fluid extractions with cosolvents of wool wax from wool scour wastes", J. Supercritical Fluids, 2005, vol. 35, pp. 235-239.
V. Eychenne et al., "Near-critical solvent extraction of wool with modified carbon dioxide—Experimental results", J. Supercritical Fluids, 2001, vol. No. 1, pp. 23-31.

* cited by examiner

*Primary Examiner* — Yate K Cutliff
(74) *Attorney, Agent, or Firm* — K&L Gates LLP

(57) ABSTRACT

A method for extracting internal lipids from wool that is substantially free of lanolin, comprising the use of a fluid under supercritical conditions and an agent that can change the polarity of said fluid, selected from methanol and/or ethanol, is disclosed. According to the operating conditions described, the temperature is between 40° C. and 120° C., and the pressure is between 120 bars and 330 bars. The polarity-changing agent represents between 3% and 15% expressed as volume/volume. The inventive method can be used to obtain internal lipids from wool, one of the most significant components of which are ceramides, which can be used in compositions intended to protect human skin against environmental damage.

20 Claims, No Drawings

METHOD FOR EXTRACTING INTERNAL LIPIDS FROM WOOL USING SUPERCRITICAL FLUIDS

CROSS REFERENCE TO RELATED APPLICATIONS AND PRIORITY CLAIM

This application claims the benefit under 35 U.S.C. §371 to PCT/ES2008/070033 filed Feb. 27, 2008, which claims the benefit of Spanish Patent Application No. P200700543 filed Mar. 1, 2007 in Spain. The entire disclosures of said applications are incorporated herein by reference thereto.

FIELD OF THE ART

The present disclosure relates to processes for extracting internal wool lipids from wool using a fluid in supercritical conditions.

BACKGROUND

Wool is a natural fibre obtained from sheep and consists mostly of protein components and minor lipid components.

Keratin proteins constitute 80% of the total fibre and are characterized by a significant content in cystine. The physical and chemical properties of wool are determined by the existence of this amino acid and by the nature and molecular weight of the lateral chains constituted by said proteins.

Despite being found in minority proportions, the lipid components of wool appear to fulfil an essential role in many of the physical-chemical properties of wool fibres. According to their position on the fibre, they can be classified into external lipids and internal lipids.

External lipids are found on the surface of wool fibres and are secreted by the animals' skin. These external lipids consist of saponifiable fats, non-saponifiable materials and traces of free inorganic acids in addition to other impurities. Lanolin is the wax obtained from wool once it has been purified, which is used for waterproofing and in skin treatment.

Various methods for extracting lanolin are described in the literature. Among these, one would cite those that use fluids in supercritical conditions, such as for example those described in Spanish patent applications ES-A-2186485 and ES-A-2161611, in patent application PCT WO-A-02/100990-A1, and in the articles by Alzaga et al., Anal. Chim. Acta, 1999, 381, 39-48, Eychenne et al., J. Supercrit. Fluids, 2001, 21, 23-31, Domínguez et al., Anal. Chim. Acta, 2003, 477, 233-242, Domínguez et al., J. Am. Oil. Chem. Soc., 2003, 80 (7), 717-724, Domínguez et al., Proceedings of the 10$^{th}$ International Wool Textile Research Conference, 2000, Aachen, and Domínguez et al., Proceedings of the 11$^{th}$ International Wool Research Conference, 2005, Leeds.

At the same time, internal lipids are found in the internal structures of the wool fibres, in what is referred to as the cellular membrane complex, in proportions that vary from 1.2% to 1.5% in relation to the total weight of the fibre.

Exhaustive analyses have been carried out and have identified free fatty acids, cholesterol, ceramides, and cholesterol sulphate as the main components of internal lipids.

One of the most valued components of internal wool lipids are ceramides, because, as described in Spanish patent application ES-A-2157807, they form a substantial part of the lipid barrier of human skin, which is responsible for protecting the same from environmental aggressions and maintaining the balanced hydration it needs for its good conservation.

In the state of the art, different methods have been used for extracting internal wool lipids. In general, the art of supercritical extraction using carbon dioxide provides extracts with a somewhat higher content in ceramides than that obtained with the conventional extraction art using mixtures of solvents; however, the performance of the extraction turns out to be lower.

Patent application ES-A-2157807, already mentioned above, describes a procedure for extracting internal wool lipids using carbon dioxide in supercritical conditions. This procedure uses wool that is substantially free of lanolin as the source material.

The extraction procedure described is carried out at a pressure of 340 atmospheres (344 bars), at a temperature of 100° C. and with 10% expressed in volume/volume of methanol as a co-solvent.

The performances of the extraction depend on the type of wool used. In the case of Spanish Merino wool, 0.290% of internal lipids are obtained over the initial weight of the extracted wool fibre, and in the case of New Zealand Merino wool, 0.355% is obtained. A quantitative analysis of the internal lipids made it possible to determine that 0.13% and 0.11% of ceramides had been extracted respectively over the total weight of extracted wool.

The article by Coderch et al., J. Am. Oil. Chem. Soc. 2002, 79 (12), 1215-1220 describes various procedures for the extraction of internal lipids from wool that is substantially free of lanolin in supercritical conditions using carbon dioxide.

In this article, different tests were carried out in varying conditions with two types of wool: Romney from New Zealand (R-NZ) and Merino from Spain (M-ES). The results of total extracted lipids, expressed as a percentage over the weight of extracted wool fibre, are summarized in the table below:

| Test | Wool | Pressure (bars) | T (° C.) | Co-solvent | % (v/v) of co-solvent | % of total lipids over weight of the wool |
|---|---|---|---|---|---|---|
| 1 | R-NZ | 360 | 60 | Methanol | 10 | 0.143 |
| 2 | R-NZ | 360 | 100 | Methanol | 10 | 0.226 |
| 3 | R-NZ | 360 | 160 | Methanol | 10 | 0.188 |
| 4 | R-NZ | 360 | 100 | Methanol | 20 | 0.125 |
| 5 | M-ES | 360 | 60 | Methanol | 10 | 0.147 |
| 6 | M-ES | 360 | 100 | Methanol | 10 | 0.202 |
| 7 | M-ES | 100 | 60 | Ethanol | 20 | 0.881 |
| 8 | M-ES | 360 | 60 | Ethanol | 20 | 0.564 |

One can see that the highest extraction performances were obtained in tests nos. 7 and 8 using a relatively high percentage of ethanol (20%) as the co-solvent.

According to the data appearing in this publication, in test no. 7 the extract contained 33% of ceramides, which represented an extraction of 0.29% of ceramides over the total weight of extracted wool. In test no. 8, the extract contained 23% of ceramides, which represented an extraction of 0.13% of ceramides over the total weight of extracted wool.

Test no. 7 has been repeated obtaining only 0.476% of total lipids over the weight of the wool, a considerably lower value to the one described in the article, and which represents an extraction of 0.18% of ceramides over the total weight of extracted wool.

Therefore, the need exists to have an extraction procedure capable of giving a better performance in obtaining the internal lipids from wool, with a high content in ceramides, and using less quantity of co-solvent as polarity-modifier of the fluid in supercritical conditions.

Thus, one object of the disclosure is a process for obtaining the internal lipids from wool fibres using wool that is substantially lanolin-free.

DETAILED DESCRIPTION OF THE PREFERRED EMBODIMENTS

An object of the disclosure are processes for obtaining internal wool lipids from substantially lanolin-free wool through extraction using a fluid in supercritical conditions and a polarity-modifying agent chosen from methanol and/or ethanol characterized in that the extraction is carried out at a temperature ranging between 40° C. and 120° C., at a pressure ranging between 120 and 330 bars, and with a content in polarity-modifying agent ranging between 3% and 15% expressed in volume/volume (v/v).

Internal Wool Lipids

Internal wool lipids are found in the internal structures of wool fibres, in the so-called cellular membrane complex, in proportions that vary from 1.2% to 1.5% in relation to the total weight of the fibre, and are described in the publication by L. Coderch et al., J. Am. Oil. Chem. Soc. 1995, 72, 715-720.

Hereinafter the internal lipids from wool will be referred to using the abbreviation IWL (Internal Wool Lipids in English).

IWL are rich in free fatty acids, cholesterol, cholesterol sulphate and ceramides, all of which are relatively polar lipid compounds.

Tests on the application of IWL to human skin demonstrate that said extracts have a remarkable capacity to reduce transepidermal water loss and to improve the skin's hydration capacity, especially in conditions of chemical or mechanical aggression to the skin, as described in Spanish patent application ES-A-2157807. Therefore, IWL obtained using the processes described herein can be profitably formulated, in varying proportions, as the essential components of pharmaceutical and/or cosmetic compositions for the care and treatment of human skin.

The extracts obtained through the disclosed processes were analysed using thin layer chromatography together with flame ionisation detection (TLC-FID), as described, for example, in the publication by L. Coderch et al., J. Plan. Chrom., 2000, 13, 119-122.

Use of this art has permitted the separation and quantification of mixtures of both simple lipids (free fatty acids, mono-, di-, and triglycerides, and sterols) as well as more complex lipids (ceramides, glycolipids, and phospholipids).

Source Product

The processes disclosed herein use substantially lanolin-free wool as the source product.

This wool can come from various breeds and varieties of sheep, such as Spanish Merino, Russian Merino, Australian Merino, South African Merino, New Zealand Merino, New Zealand Romney, etc., and is subject to a process of eliminating surface lipids by means of well-known arts of washing with detergents or as described, for example, in U.S. Pat. No. 3,619,116, or in Spanish patent application A-2157807.

Supercritical Fluid

The disclosed processes use a fluid in supercritical conditions for the extraction of IWL.

A fluid in supercritical conditions is a fluid whose temperature and pressure conditions are above its critical thermodynamic point. Such fluid has the capacity to diffuse in solids as if it were a gas, and to dissolve solids as if it were a liquid.

Among the fluids used in supercritical conditions we find, for example, carbon dioxide, water, acetone, ethanol and methanol.

The processes disclosed herein preferably use carbon dioxide.

Carbon dioxide is found in supercritical conditions when the temperature is above 31° C. and the pressure is above 74 bars (73 atmospheres). This gas offers the benefit of low toxicity and environmental impact. Plus it is a non-flammable and non-explosive gas and can be found commercially with a high purity at a relatively low price.

The use of carbon dioxide in supercritical conditions makes it possible to reduce the volume of organic solvents used.

A suitable carbon dioxide for carrying out the processes described is sold, for example, by the company Abelló Linde (Barcelona, Spain).

Polarity-Modifying Agent

The disclosed processes use a polarity modifier chosen from methanol and/or ethanol, which improves the performance of the IWL extraction.

Preferably, methanol is used.

In supercritical state, carbon dioxide has an adequate polarity for extracting compounds of a lipophilic nature. But it has difficulties in extracting polar compounds, such as ceramides. Therefore, these agents that modify the polarity of carbon dioxide are introduced in order to improve the performance of the extraction of the most polar compounds.

In the disclosed processes, the content in polarity-modifying agent ranges between 3% and 15% expressed in volume/volume, preferably between 4% and 12%, and more preferably between 5% and 10%.

The content in the polarity-modifying agent is expressed as a percentage in volume over the volume of carbon dioxide employed.

Extraction Conditions

In the processes described herein, the extraction is carried out at a temperature ranging between 40° C. and 110° C., preferably between 50° C. and 100° C., more preferably between 60° C. and 90° C., and at pressure ranging between 140 and 330 bars, preferably between 150 and 310 bars, more preferably between 160 and 300 bars.

More preferably, the extraction is carried out at a temperature ranging between 60° C. and 90° C., at a pressure ranging between 160 and 300 bars, and with a content in polarity-modifying agent ranging between 7.5% and 12.5% expressed in volume/volume.

Extraction Equipment and Operational Procedure

IWL extractions can be carried out on a laboratory scale using analytical equipment such as, for example, the desktop equipment SUPREXPREPMASTER (Suprex, US), on a pilot plant scale with equipment, for example, of Iberfluids Instruments (Barcelona, Spain), or also on an industrial scale.

In the event of carrying out an extraction with carbon dioxide using laboratory equipment such as that mentioned above for example, the operational procedure is as follows.

A quantity of approximately 8 to 12 g of prepared wool is introduced in the extraction cell, which may have a volume ranging between 40 and 60 mL. The cell is sealed after fitting the corresponding filter and join, and the cell is connected to the equipment.

Usually, the equipment includes software that can be used to set the required extraction conditions: temperature, pressure, percentage of polarity-modifying agent, and volume of carbon dioxide.

The carbon dioxide is released from the gas supply bottle and is pumped into the system by means of two pistons in series until the required working pressure is reached. Mean-while, the air that surrounds the extraction cell is heated using two electrical resistances until the cell shows the established working temperature.

Once the required pressure and temperature are reached, the carbon dioxide retreats to the pump outlet of the polarity-modifying agent, for automatic dosing of same, and they are mixed.

Usually, a volume of carbon dioxide is used that ranges between 3 and 7 times the cell volume. It has been observed that variations in said volume do not have a substantial impact on the performance of the extraction.

The mixture of carbon dioxide and polarity-modifying agent is introduced in the extraction cell, where it diffuses into the wool, and extracts the soluble lipids in the operational conditions established in the test.

The extraction fluid, which contains the compounds of interest, leaves the extraction cell and is led to a collection module, which consists of a test tube, previously weighed with septum (Supelco, Bellefonte, US). Said test tube has an inlet and an outlet for eliminating the decompressed carbon dioxide, and depressurization occurs here until reaching atmospheric pressure through a fixed flow capillary tube of 1.5 mL/min.

The liquid sample collected in the test tube is usually concentrated until dry under a current of nitrogen.

The extracted IWL are quantified through gravimetry, diluted in a mixture of chloroform/methanol (2:1 in v/v) and conserved in a nitrogen atmosphere at a temperature of approximately −20° C., until the time of their analysis, following the methods already mentioned above.

Surprisingly, it was observed that the choice of operational parameters that characterize the processes permits a high performance extraction of the IWL, with a high content in ceramides.

Despite working with a relatively low content in polarity-modifying agent, IWL extracts were obtained with a significant content in ceramides.

With these processes it has been possible to obtain up to 0.85% of IWL over the weight of extracted wool fibre, with a ceramides content of 42% in weight, representing 0.36% of ceramides over the weight of extracted wool fibre. Usually, average values of extracted IWL of 0.70% over the weight of extracted wool fibre are obtained, and average values of extracted ceramides of 0.27% over the weight of extracted wool fibre.

In the prior art mentioned previously, the highest values of ceramides were around 0.18% over the weight of extracted wool fibre, representing a 1.5 to 2 times lower performance than that obtained using the processes of this disclosure.

It will be apparent to those skilled in the art that various modifications and variations can be made to the disclosure and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted, to limit the scope of the invention.

EXAMPLES

Example 1

Prior Preparation of the Wool Fibres

Wool is obtained from live sheep using physical shearing, and then surface grease, also known as lanolin, is eliminated through industrial washing, generally in wash trains consisting of 5 washing tubs. The washing sequence has consisted of a first wash in water at a temperature ranging between 35° C. and 40° C. ($1^{st}$ tub), followed by a treatment with sodium carbonate at a temperature ranging between 45° C. and 55° C. ($2^{nd}$ tub), a mixture of sodium carbonate and ethoxylated nonilphenol with 8 to 9 moles of ethylene oxide at a temperature ranging between 50° C. and 58° C. ($3^{rd}$ tub), ethoxylated nonilphenol with 8 to 9 moles of ethylene oxide at a temperature ranging between 50° C. and 52° C. ($4^{th}$ tub) and a final rinse with water at a temperature ranging between 45° C. and 47° C. ($5^{th}$ tub). Finally, the wool fibres are dried in room temperature and humidity conditions, concluding with a preparatory treatment lasting 24 hours at 20° C. and with a relative humidity of 60%.

Example 2

Process for Extracting IWL with Carbon Dioxide in Supercritical Conditions Using Analytical Equipment SUPREX-PREPMASTER analytical extraction apparatus was used. This apparatus distributed the carbon dioxide (high purity, Abelló Linde, Barcelona, Spain) from the bottle supplying the extraction cell using a system of two pistons in series, in such a way that while one of the pistons was pumping and compressing the carbon dioxide that went to the extraction system, the second piston was in the filling stage.

The polarity modifier (methanol, analytical grade, Merck, Darmstad, Germany) was supplied through a pump of the SUPREX brand (MPA-1) in the proportion specified below. The extract was gathered through decompression of the carbon dioxide in a test tube through a fixed flow capillary tube (1.5 ml/min).

10 g of prepared wool obtained as per Example 1 were introduced in the cell of 50 mL in volume, where the extraction took place in supercritical conditions by means of carbon dioxide. The conditions were: 162 bars, 60° C. temperature and 10% v/v in (v/v) of methanol. The temperature was reached by heating the air surrounding the extraction cell using two electrical resistances.

The total volume of liquid used for the extraction was 5 times the volume of the cell, in other words 250 mL. The carbon dioxide loaded with the extract left the system through a fixed flow capillary (1.5 mL/min), the precipitation of the internal wool lipids occurring together with the modifier in the sample collection test tube.

The test tube with septum (Supelco, Bellefonte, US) had a 20 mL capacity and was previously weighed. This test tube had an outlet for removing the decompressed carbon dioxide, and the sample, in liquid form, was concentrated until dry under a current of nitrogen.

The extracted internal wool lipids were quantified using the gravimetry method and were re-suspended in chloroform/methanol 2:1 (1 mL), maintained at nitrogen refrigeration temperature and atmosphere.

Internal wool lipids of 0.741% over the weight of wool were obtained, containing 40.1% in weight of ceramides, corresponding to 0.297% of ceramides over the weight of extracted wool.

Examples 3-14

Process for Extracting IWL with Carbon Dioxide in Supercritical Conditions Using Analytical Equipment Following a similar process to the one described in Example 2, extraction tests were carried out in the conditions that appear in Table I. The results express the percentage of extracted IWL and ceramides over the total weight of extracted wool fibre:

TABLE I

| Example | T (° C.) | P (bars) | Modifier (%, type) | Total volume (ml) | IWL (%) | Ceramides (%) |
|---|---|---|---|---|---|---|
| 3 | 40 | 162 | 5, MeOH | 200 | 0.624 | 0.226 |
| 4 | 40 | 253 | 10, MeOH | 300 | 0.556 | 0.230 |
| 5 | 50 | 253 | 7.5, MeOH | 200 | 0.600 | 0.227 |
| 6 | 60 | 233 | 10, MeOH | 350 | 0.704 | 0.296 |
| 7 | 60 | 304 | 10, MeOH | 250 | 0.858 | 0.296 |
| 8 | 75 | 304 | 10, MeOH | 150 | 0.851 | 0.356 |
| 9 | 90 | 233 | 10, MeOH | 350 | 0.803 | 0.297 |
| 10 | 90 | 304 | 10, MeOH | 250 | 0.818 | 0.278 |
| 11 | 75 | 304 | 10, MeOH | 350 | 0.823 | 0.297 |
| 12 | 60 | 162 | 7.5, MeOH | 300 | 0.560 | 0.233 |
| 13 | 40 | 202 | 7.5, MeOH | 250 | 0.550 | 0.232 |
| 14 | 60 | 162 | 10, EtOH | 350 | 0.618 | 0.249 |

One can see how in the operational conditions of the described processes notable performances in IWL are obtained, and in particular in ceramides in relation to the total weight of extracted wool.

Example 15

Process for Extracting IWL Through Carbon Dioxide in Supercritical Conditions Using a Pilot Plant The pilot plant used to carry out the supercritical extraction distributes the carbon dioxide (high purity, Abelló Linde, Barcelona, Spain) from the supply bottle to the extraction cell using an alternative positive displacement pump with a MIL-ROYAL D membrane head (Type MD-140G-6-M-390/J) with external cooling.

The polarity modifier (methanol, analytical grade, Merck, Darmstad, Germany) was supplied through an alternative positive displacement pump according to the established proportion.

The flow of carbon dioxide in supercritical conditions could reach a maximum of 3500 mL/h depending on the extraction pressure. During the test, the flow was kept between 1500-1800 mL/h.

50 g of prepared wool obtained as per Example 1 were introduced in the cell (375 mL) where the extraction took place using carbon dioxide in supercritical conditions. The conditions were: 162 bars, 60° C. temperature and 10% of methanol. The total volume of the liquid used for the extraction was 5 times the cell volume.

The extract was collected in three separators, following a depressurization phase in three stages using servomotorised regulation microvalves. The conditions of the three stages were as follows: 122 bars and 60° C. in the first separator, 61 bars and 60° C. in the second separator, and atmospheric conditions in the third separator. The carbon dioxide in gaseous phase left the system through a mass flow meter.

The extract was dried first in the SAVANT SPEEDVAC-PLUS SC 210 A vacuum concentrator (Thermoquest), and finally with a nitrogen current, with a view to eliminating any remains of solvent.

The extracted IWL was quantified by gravimetry and re-suspended in chloroform/methanol 2:1 (1 or 5 mL), maintaining nitrogen refrigeration temperature and atmosphere.

The weight in lipids obtained was 0.64% over the weight of extracted wool fibre, which contained 37% in weight of ceramides, meaning that 0.237% in weight of ceramides over the weight of extracted wool was obtained.

Having sufficiently described the nature of the various example embodiments, it should be stated that the aforementioned processes and devices used therein may have their details modified provided it does not alter the fundamental principle.

The invention is, of course, not limited to the examples described but cover all the variants defined in the claims. The terms "a" and "an" and "the" and similar referents used in the context of the following claims are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g. "such as") provided herein is intended merely to better illuminate the embodiments and does not pose a limitation on the scope of the embodiments otherwise claimed. No language in the specification should be construed as indicating any non-claimed element essential to the practice of the embodiments.

The use of the term "or" in the claims is used to mean "and/or" unless explicitly indicated to refer to alternatives only or the alternatives are mutually exclusive, although the disclosure supports a definition that refers to only alternatives and "and/or." Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments are described herein, including the best mode known to the inventors for carrying out the invention. Of course, variations on those preferred embodiments will become apparent to those of ordinary skill in the art upon reading the foregoing description. The inventors expect those of ordinary skill in the art to employ such variations as appropriate, and the inventors intend for the embodiments to be practiced otherwise than specifically described herein. Accordingly, these embodiments include all modifications and equivalents of the subject matter recited in the claims appended hereto as permitted by applicable law. Moreover, any combination of the above-described elements in all possible variations thereof are encompassed by the embodiments unless otherwise indicated herein or otherwise clearly contradicted by context.

Further, it is to be understood that the example embodiments disclosed herein are illustrative. Other modifications that may be employed are within the scope of the embodiments. Thus, by way of example, but not of limitation, alternative configurations of the present embodiments may be utilized in accordance with the teachings herein. Accordingly, the present embodiments are not limited to that precisely as shown and described herein.

The invention claimed is:

1. A process for obtaining internal wool lipids from substantially lanolin-free wool comprising extracting the lipids from the wool with a fluid in supercritical conditions and a polarity-modifying agent,
wherein the polarity-modifying agent is at least one of methanol and ethanol, and wherein said extraction is carried out at a temperature between about 40° C. and about 120° C., at a pressure between about 120 bars and about 330 bars, and with a content in polarity-modifying agent between about 3% and about 15% relative to the supercritical fluid.

2. The process of claim 1, wherein the supercritical fluid is at least one of carbon dioxide, water, acetone, ethanol, and methanol.

3. The process of claim 2, wherein the supercritical fluid is carbon dioxide.

4. The process of claim 1, wherein the polarity-modifying agent is methanol.

5. The process of claim 1, wherein the polarity-modifying agent is ethanol.

6. The process of claim 1, wherein the content in polarity-modifying agent is between about 4% and about 12%.

7. The process of claim 6, wherein the content in polarity-modifying agent is between about 5% and about 10%.

8. The process of claim 1, wherein said extraction is carried out at a temperature between about 50° C. and about 100° C.

9. The process of claim 8, wherein said extraction is carried out at a temperature between about 60° C. and about 90° C.

10. The process of claim 1, wherein said extraction is carried out at a pressure between about 150 bars and about 310 bars.

11. The process of claim 10, wherein said extraction is carried out at a pressure between about 160 and about 300 bars.

12. The process of claim 1, wherein said extraction is carried out at a temperature between about 60° C. and about 90° C., at a pressure between about 160 bars and 300 bars, and with a content in polarity-modifying agent between about 7.5% and 12.5%.

13. The process of claim 3, wherein the polarity-modifying agent is ethanol.

14. The process of claim 13, wherein the ethanol content is between about 5% and about 10%.

15. The process of claim 14, wherein said extraction is carried out at a temperature between about 60° C. and about 90° C.

16. The process of claim 15, wherein said extraction is carried out at a pressure between about 160 and about 300 bars.

17. The process of claim 3, wherein the polarity-modifying agent is methanol.

18. The process of claim 17, wherein the methanol content is between about 5% and about 10%.

19. The process of claim 18, wherein said extraction is carried out at a temperature between about 60° C. and about 90° C.

20. The process of claim 19, wherein said extraction is carried out at a pressure between about 160 and about 300 bars.

* * * * *